(12) United States Patent
Yu

(10) Patent No.: US 7,708,881 B2
(45) Date of Patent: May 4, 2010

(54) MAGNETIC BEAD-BASED SAMPLE SEPARATING DEVICE

(75) Inventor: Tung-Ming Yu, Su-ao Township, Yilan County (TW)

(73) Assignee: Industrial Technology Research Institute, Hsinchu (TW)

( * ) Notice: Subject to any disclaimer, the term of this patent is extended or adjusted under 35 U.S.C. 154(b) by 796 days.

(21) Appl. No.: 11/646,337

(22) Filed: Dec. 28, 2006

(65) Prior Publication Data

US 2008/0031787 A1 Feb. 7, 2008

(30) Foreign Application Priority Data

Aug. 2, 2006 (TW) .............................. 95128385 A

(51) Int. Cl.
*B01D 35/06* (2006.01)
*G01N 33/553* (2006.01)
*G01N 35/08* (2006.01)

(52) U.S. Cl. .................. 210/222; 436/52; 436/177; 436/526; 422/101; 422/186.01; 422/188; 422/189; 210/695

(58) Field of Classification Search .................. 436/52, 436/177, 526; 422/101, 186.01, 188, 189; 210/222, 695
See application file for complete search history.

(56) References Cited

U.S. PATENT DOCUMENTS

| 6,129,848 | A | 10/2000 | Chen et al. |
| 6,187,270 | B1 | 2/2001 | Schmitt et al. |
| 6,291,249 | B1 | 9/2001 | Mahant et al. |
| 6,468,810 | B1 | 10/2002 | Korpela |
| 6,514,415 | B2 | 2/2003 | Hatch et al. |

*Primary Examiner*—David A Reifsnyder
(74) *Attorney, Agent, or Firm*—Rabin & Berdo, P.C.

(57) ABSTRACT

A magnetic bead-based sample separating device is provided. The device includes a first reactor, a second reactor, a third reactor, a first micro-channel and a second micro-channel. The first reactor receives a mixing solution including several magnetic beads and a sample extraction. The sample extraction is bound with the magnetic beads. The second reactor receives a washing buffer for washing the magnetic beads with sample extraction. The third reactor receives an elution buffer for separating the washing buffer from the magnetic beads. The first micro-channel is for connecting the first reactor and the second reactor and moving the magnetic beads to the second reactor from the first reactor. The second micro-channel is for connecting the second reactor and the third reactor and moving the magnetic beads to the third reactor from the second reactor.

20 Claims, 8 Drawing Sheets

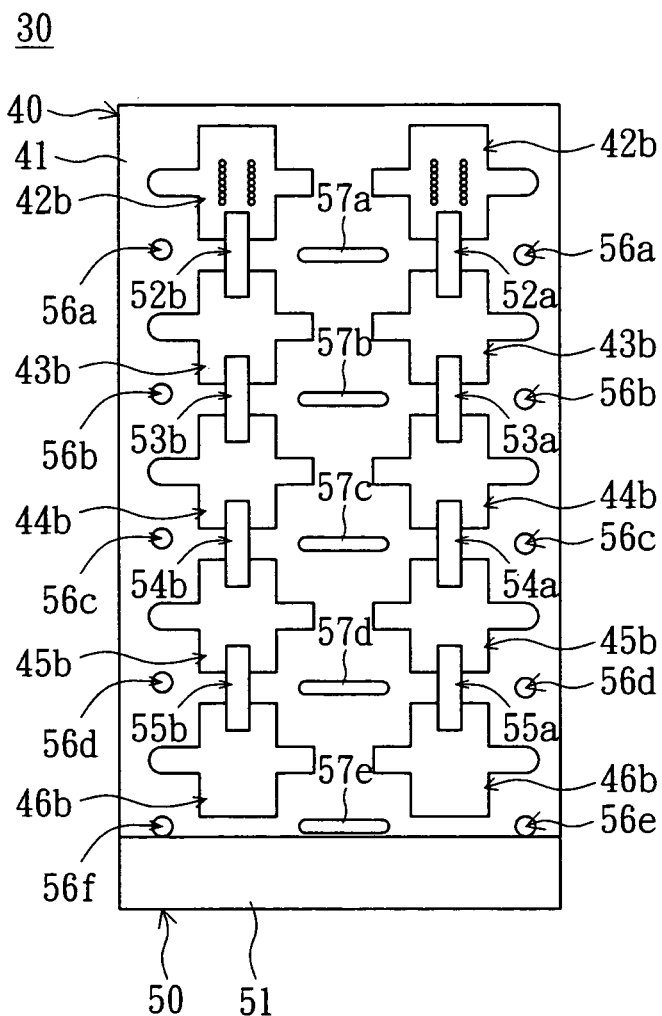
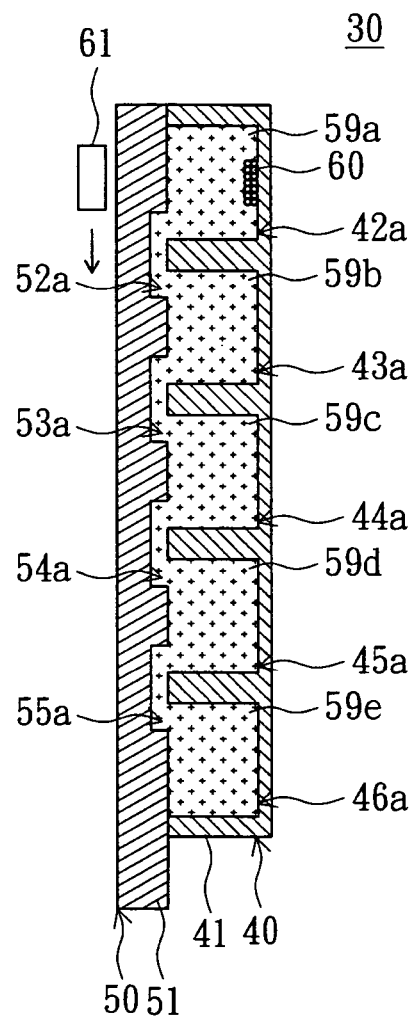
FIG. 7A
FIG. 7B
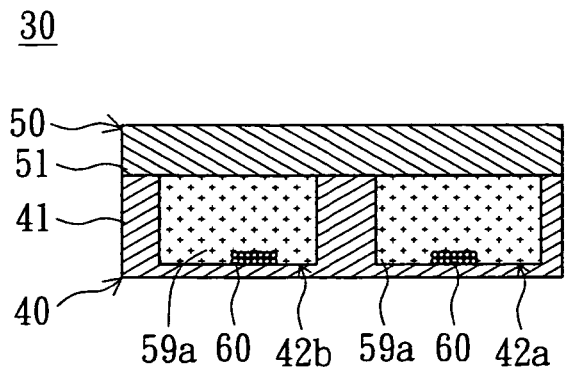
FIG. 7C

MAGNETIC BEAD-BASED SAMPLE SEPARATING DEVICE

This application claims the benefit of Taiwan application Serial No. 95128385, filed Aug. 2, 2006, the subject matter of which is incorporated herein by reference.

BACKGROUND OF THE INVENTION

1. Field of the Invention

The invention relates in general to a magnetic bead-based sample separating device, and more particularly to a magnetic bead-based sample separating device using a multiple serial reactor and a misplaced micro-channel net movement.

2. Description of the Related Art

Magnetic bead-based separating technology has been widely used in immunoassays, particularly, in the analysis of sample extraction of protein, deoxyribonucleic acid (DNA) and ribonucleic acid (RNA). The magnetic bead-based separating technology has two ways of operations: one is through manual operation and the other is mechanical operation using automatic apparatus.

In terms of manual operation, referring to FIG. 1, a flowchart of separating sample extraction by magnetic beads according to U.S. Pat. No. 6,187,270B1 is shown. Firstly, a mixing solution 11 is added to a tube 16. The mixing solution 11 includes several magnetic beads 15, and the sample extraction is bound on the surface coating of the magnetic beads 15. Next, a magnetic iron 14 is used to attract the magnetic beads 15 with sample extraction and suck the solution out from the tube 16. Then, a washing buffer 12 is added to the tube 16 for washing the impurities attached on the magnetic beads 15 with sample extraction. Next, the magnetic iron 14 is used to attract the magnetic beads 15 with sample extraction and suck the solution out from the tube 16. It is noted that the step of washing the magnetic beads 15 with sample extraction by the washing buffer 12 can be flexibly prolonged according to the state of cleaning. Then, the elution buffer 13 is added to the tube 16 for separating the sample extraction from the magnetic beads 15. Next, the magnetic iron 14 is used to attract the magnetic beads 15 and suck the solution out from the tube 16 to obtain a sample extracting solution.

However, the steps of binding the sample extraction on the magnetic beads 15, quantifying reactive reagent, sucking and adding solution, and then separating the sample extracting solution from the magnetic beads 15 are all done manually, not only labor consuming but also requiring lots of operating time.

Referring to U.S. Pat. No. 6,468,810B1, the magnetic beads enable the magnetic iron to suck the connected cells such as the sample extraction at the bottom of the tube via the compression of spring. Meanwhile, several tubes are purified and cleaned inside the corresponding tube. Lastly, the spring is released, such that the magnetic iron is released from the bottom of the tube to separate the magnetic beads for the extraction. Similarly, the operating procedures are still complicated and the operating time is long and tedious.

In terms of mechanical operation through automatic apparatus, all the procedures are automatically processed, such that the labor and operating time are saved and several samples can be processed at the same time. Despite the automatic apparatus produces more sample extraction, however, the automatic apparatus is expensive and uneconomical, and occupies a large volume of space.

SUMMARY OF THE INVENTION

It is therefore an object of the invention to provide a magnetic bead-based sample separating device. Serial reactors are used to carry the reactive reagent for separating the magnetic beads. The reactors are connected by a micro-channel, and a magnetic iron is used to provide a magnetic force for moving the magnetic beads from the first reactor to the second reactor via the micro-channel. The rest may be performed by analogy such that the entire magnetic bead-based sample extracting process is completed. Besides, the magnetic bead-based sample separating device of the invention can further integrate multiple serial reactors into an array and use the misplaced micro-channel net movement, provide synchronous filling for multiple reactive reagents, and can be started up synchronously with the serial reactor array. Therefore, the magnetic bead-based sample separating device of the invention employs multiple serial reactors and the misplaced micro-channel net movement, and is capable of adding the reagent and completing the magnetic bead-based sample extracting process synchronously. Consequently, the magnetic beads extracting rate is increased, and the extraction of magnetic beads is enhanced. Besides, the process of the invention is performed at an enclosed space, largely reducing pollution risk.

The invention achieves the above-identified object by providing a magnetic bead-based sample separating device. The device includes a body, a first reactor, a second reactor, a third reactor, a first micro-channel and a second micro-channel. The first reactor, the second reactor and the third reactor are disposed inside the body. The first reactor is for receiving a mixing solution at least including several magnetic beads and a sample extraction. The sample extraction is bound with the magnetic beads. The second reactor is for receiving a washing buffer. The third reactor is for receiving an elution buffer. The second reactor is positioned between the first reactor and the third reactor. The first micro-channel and the second micro-channel are disposed inside the body. The first micro-channel is for connecting the first reactor and the second reactor. The second micro-channel is for connecting the second reactor and the third reactor. The magnetic beads are driven by a magnetic force to move to the second reactor from the first reactor via the first micro-channel for enabling the washing buffer to wash the magnetic beads. The magnetic beads are driven by a magnetic force to move to the third reactor from the second reactor via the second micro-channel such that the elution buffer separates the magnetic beads from the sample extraction.

The invention further achieves the above-identified object by providing a magnetic bead-based sample separating device. The device includes a reactor array base and a micro-channel array cover. The reactor array base includes a base body, more than two first reactors, more than two second reactors, and more than two third reactors. The more than two first reactors, the more than two second reactors, and the more than two third reactors are disposed on the base body and horizontally spaced in an equal distance. The more than two first reactors, the more than two second reactors, and the more than two third reactors are correspondingly and vertically aligned. Each second reactor is positioned between the first reactor and the third reactor. The micro-channel array cover is slideably coupled with the reactor array base and includes a cover body, more than two first micro-channels, more than two second micro-channels, and more than three third micro-channels. The cover body has a first opening, a second opening, and more than two third openings. The first reactor and the second reactor are respectively connected with the first opening and the second opening. The more than two third reactors are correspondingly connected with the more than two third openings. The more than two first micro-channels, the more than two second micro-channels, and the more than three third micro-channels are disposed on the cover body, and are horizontally spaced in an equal distance. The more than two first micro-channels and the more than two second micro-channels are correspondingly and vertically aligned. The two adjacent more than three third micro-channels are respectively positioned between the more than two first micro-channels and between the more than two second micro-channels. The three third micro-channels are respectively connected with the more than two first reactors, the more than two second reactors and the more than two third reactors. The more than two first reactors receive a mixing solution at least including several magnetic beads and a sample extraction via the first opening and the third micro-channel. The sample extraction is bound with the magnetic beads. The more than two second reactors receive a washing buffer via the second opening and the third micro-channel. The more than two third reactors receive an elution buffer via the third opening and the third micro-channel. When the micro-channel array cover and the reactor array base are relatively moved for a distance, each first micro-channel connects the adjacent first reactor and second reactor, and each second micro-channel connects the adjacent second reactor and third reactor. The third micro-channel is incapable of respectively connecting the more than two first reactors, the more than two second reactors and the more than two third reactors. The magnetic beads are driven by a magnetic force to move to the more than two second reactors from the more than two first reactors via the more than two first micro-channels such that the washing buffer washes the magnetic beads. The magnetic beads are driven by a magnetic force to move to the more than two third reactors from the more than two second reactors via the more than two second micro-channels such that the elution buffer separates the sample extraction from the magnetic beads.

Other objects, features, and advantages of the invention will become apparent from the following detailed description of the preferred but non-limiting embodiments. The following description is made with reference to the accompanying drawings.

BRIEF DESCRIPTION OF THE DRAWINGS

FIG. 7A is a top view showing the state of the magnetic bead-based sample separating device in FIG. 6A after the base and the cover are relatively moved for a distance;

FIG. 7B is a vertical cross-sectional view of a magnetic bead-based sample separating device in FIG. 7A;

FIG. 7C is a horizontal cross-sectional view of a magnetic bead-based sample separating device in FIG. 7A.

DETAILED DESCRIPTION OF THE INVENTION

First Embodiment

Figure 1:
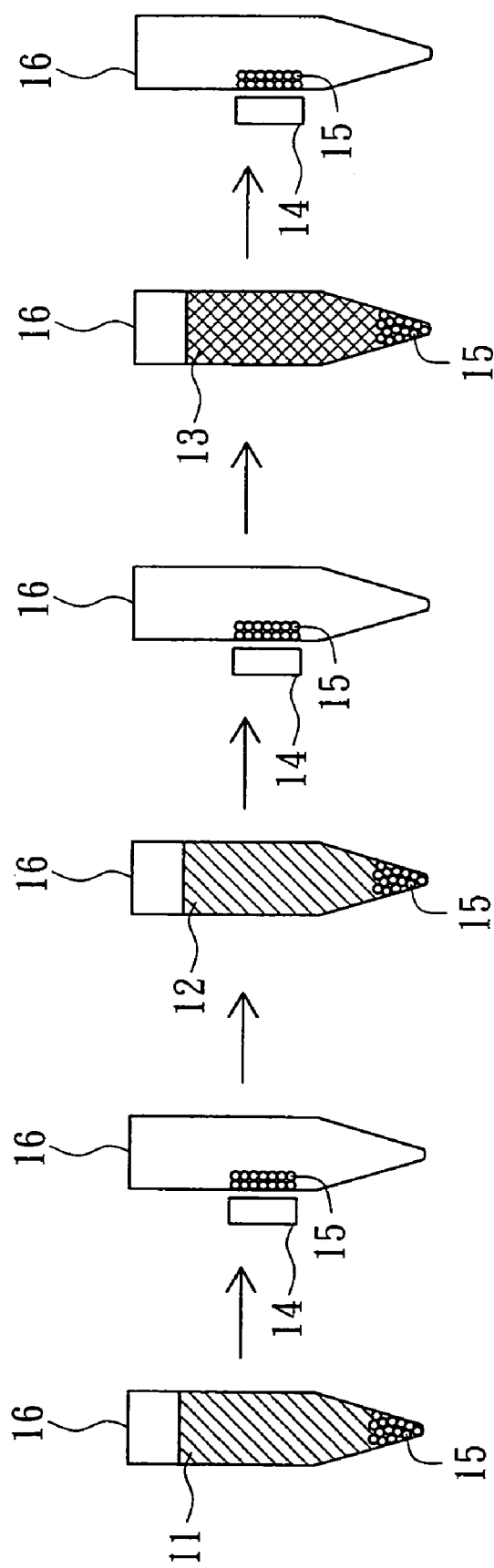
FIG. 1 (Prior Art) is a flowchart of separating sample extraction by magnetic beads according to U.S. Pat. No. 6,187,270B1.
Figure 2A:
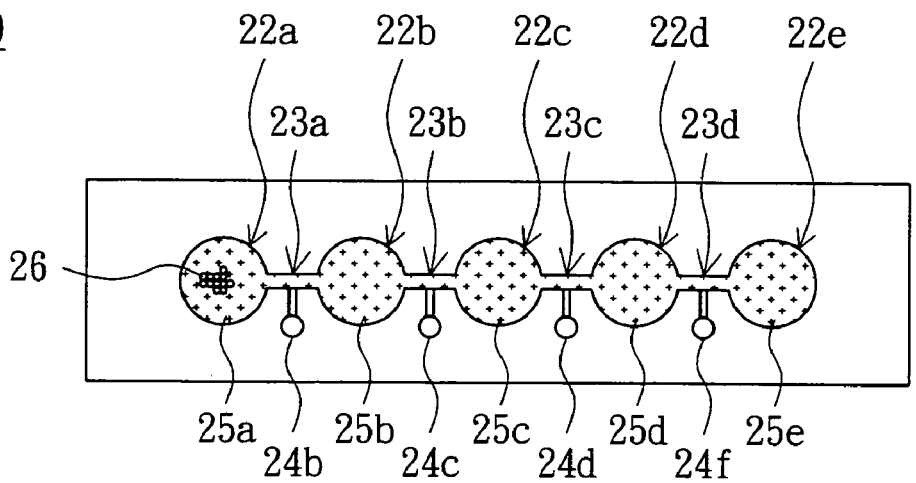
FIG. 2A is a top view of a magnetic bead-based sample separating device according to a first embodiment of the invention.
Figure 2B:
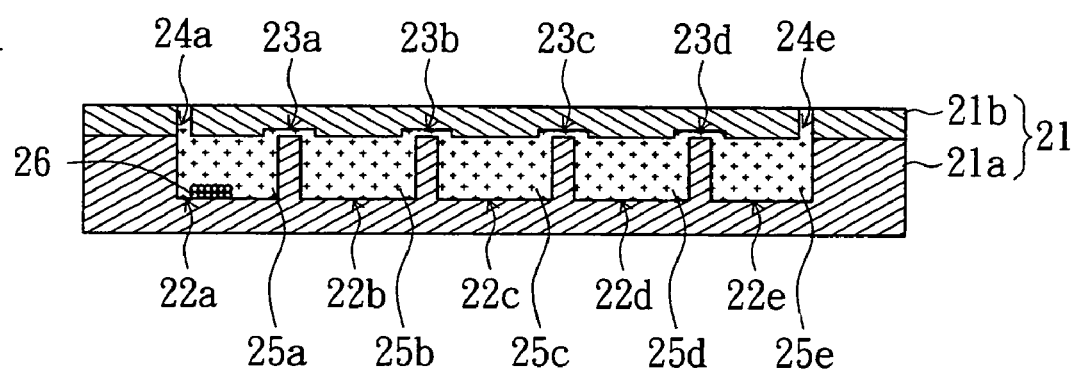
FIG. 2B is a horizontal cross-sectional view of a magnetic bead-based sample separating device in FIG. 2A.

Referring to both FIGS. 2A and 2B, FIG. 2A is a top view of a magnetic bead-based sample separating device according to a first embodiment of the invention, and FIG. 2B is a horizontal cross-sectional view of a magnetic bead-based sample separating device in FIG. 2A. The magnetic bead-based sample separating device 20 includes a body 21, five reactors 22a~22e and four micro-channels 23a~23d. The body 21 has six openings 24a~24f. The reactors 22a~22e are disposed in the body 21. The reactor 22a, exemplified by the first reactor, is used for receiving a mixing solution 25a. The mixing solution 25a at least includes several magnetic beads 26 and a sample extraction. The sample extraction is bound with the magnetic beads 26. The reactor 22b, exemplified by the second reactor, is used for receiving a washing buffer 25b. The reactor 22c is used for receiving a washing buffer 25c. The reactor 22d is used for receiving a washing buffer 25d. The reactor 22e, exemplified by the third reactor, is used for receiving an elution buffer 25e. In FIGS. 2A~2B, the reactors 22a~22e are sequentially arranged in the body 21 from left to right. The reactors 22b~22d are positioned between the reactor 22a and the reactor 22e. The reactor 22c is positioned between the reactor 22b and the reactor 22d.

The micro-channels 23a~23d are sequentially disposed in the body 21 in an equal distance. Moreover, the micro-channels 23a~23d are respectively connected to the openings 24b, 24c, 24d and 24f. The micro-channel 23a, exemplified by the first micro-channel, is for connecting the reactors 22a and 22b for allowing the magnetic beads 26 to pass through. The micro-channel 23b, exemplified by the second micro-channel, is for connecting the reactors 22b and 22c for allowing the magnetic beads 26 to pass through. The micro-channel 23c is for connecting the reactors 22c and 22d for allowing the magnetic beads 26 to pass through. The micro-channel 23d is for connecting the reactors 22d and 22e for allowing the magnetic beads 26 to pass through. Therefore, given that the openings 24c~24f are temporarily sealed, the reactor 22a is still capable of receiving the mixing solution 25a via either of the opening 24a (the first opening) and the opening 24b.

Given that the opening 24a and the openings 24d~24f are temporarily sealed, the reactor 22b is still capable of receiving the washing buffer 25b via either of the opening 24b (the second opening) and the opening 24c. Given that the opening 24a and the openings 24b and 24e~24f are temporarily sealed, the reactor 22c is still capable of receiving the washing buffer 25c via either of the openings 24c and 24d. Given that the opening 24a~24c and 24f are temporarily sealed, the reactor 22d is still capable of receiving the washing buffer 25d via either of the openings 24d and 24e. Given that the opening 24a~24d are temporarily sealed, the reactor 22e is still capable of receiving the elution buffer 25e via either of the opening 24e (the third opening) and the opening 24f. However, the ways of receiving the mixing solution 25a, the washing buffer 25b~25d and the elution buffer 25e by the reactors 22a~22e respectively are not limited to the above disclosure, and any other ways of receiving are applicable to the present embodiment of the invention. In the present embodiment of the invention, the micro-channel 23a is positioned between the apex of the reactor 22a and the apex of the reactor 22b. The micro-channel 23b is positioned between the apex of the reactor 22b and the apex of the reactor 22c. The micro-channel 23c is positioned between the apex of the reactor 22c and the apex of the reactor 22d. The micro-channel 23d is positioned between the apex of the reactor 22d and the apex of the reactor 22e. Besides, the pipe diameter of each of the micro-channels 23a~23d is larger than the diameter of each of the magnetic beads 26. The pipe diameter of each of the micro-channels 23a~23d approximately ranges between 50 μm~500 μm, and the diameter of each of the magnetic beads approximately ranges between 50 nanometer (nm)~40 μm.

Figure 3A:
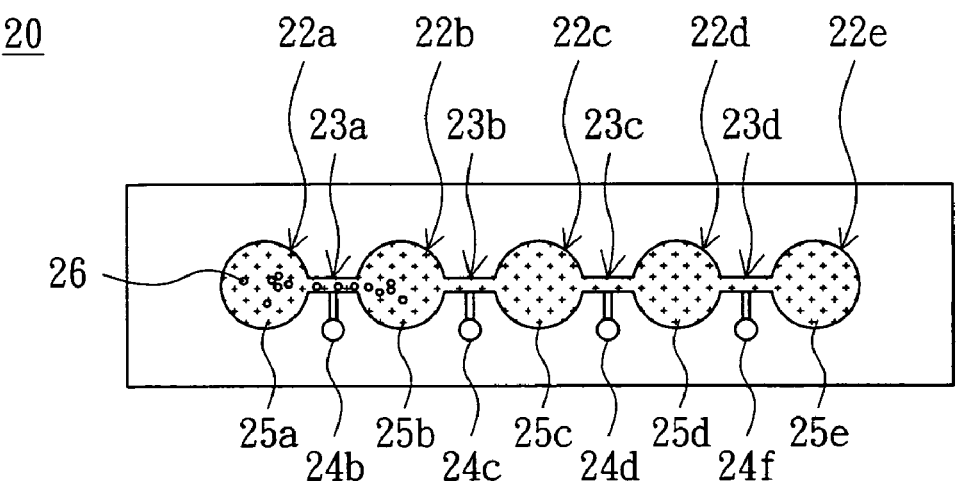
FIG. 3A is a top view showing the state of a magnetic beads of the magnetic bead-based sample separating device in FIG. 2A after entering a second reactor from a first reactor via a micro-channel.
Figure 3B:
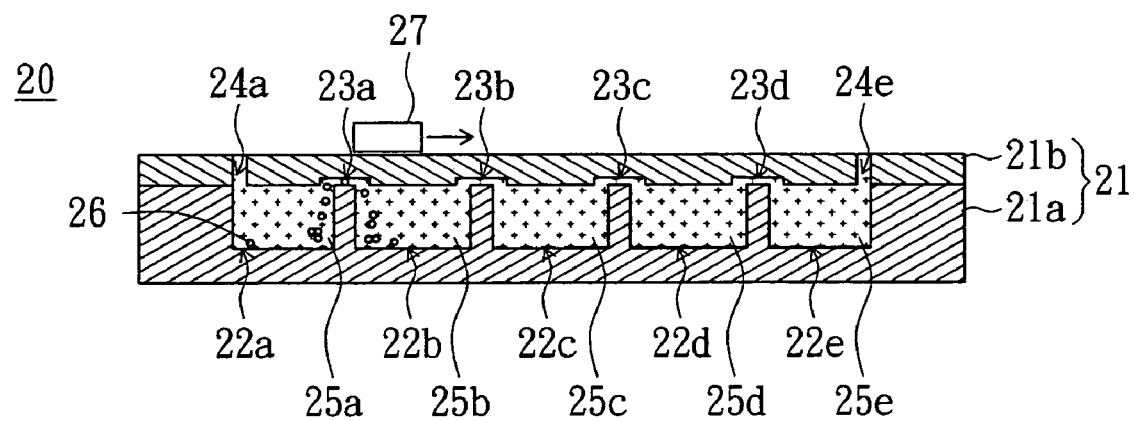
FIG. 3B is a horizontal cross-sectional view of a magnetic bead-based sample separating device in FIG. 3A.
Figure 4A:
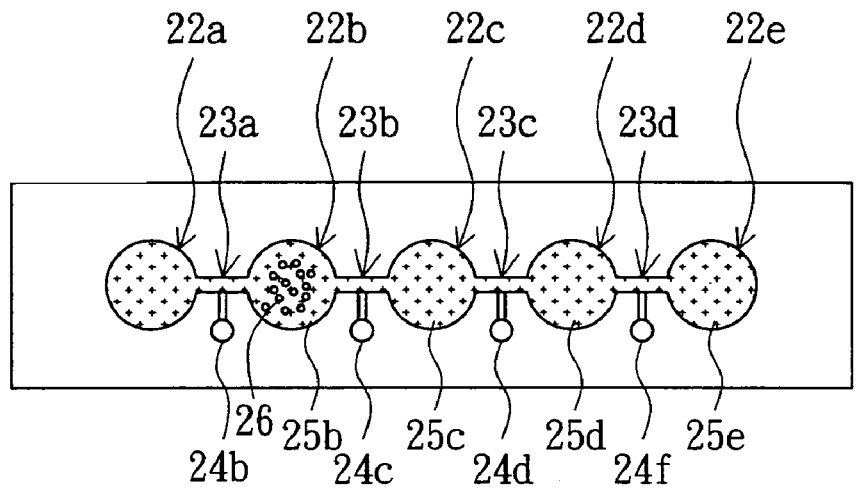
FIG. 4A is a top view showing the state of a magnetic beads of the magnetic bead-based sample separating device in FIG. 3A after having been moved to a second reactor.
Figure 4B:
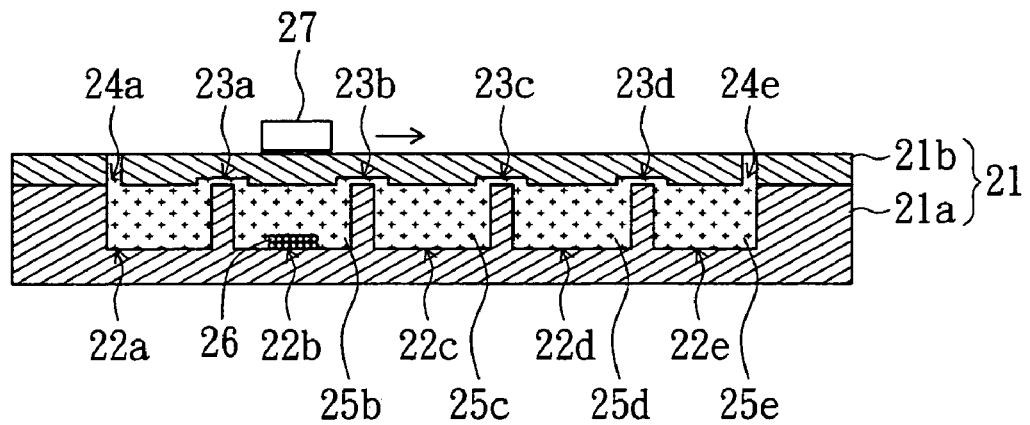
FIG. 4B is a horizontal cross-sectional view of a magnetic bead-based sample separating device in FIG. 4A.

As shown in FIGS. 3A~3B, the magnetic beads 26 with sample extraction are driven by a magnetic force to move to the reactor 22b from the reactor 22a via the micro-channel 23a, wherein the sample extraction is moved to the reactor 22b along with the magnetic beads 26, and the magnetic force is exemplified by a force provided by a magnetic iron 27. As shown in FIGS. 4A~4B, the washing buffer 25b washes the magnetic beads 26, and the impurities attached on the magnetic beads 26 are washed for the first time. The rest may be performed by analogy the magnetic beads 26 with sample extraction are driven by the above magnetic force to move to the reactor 22c from the reactor 22b via the micro-channel 23b, such that the washing buffer 25c washes the magnetic beads 26, and the impurities attached on the magnetic beads 26 are washed for the second time. Next, the magnetic beads 26 with sample extraction are driven by the above magnetic force to move to the reactor 22d from the reactor 22c via the micro-channel 23c, such that the washing buffer 25d washes the magnetic beads 26 and the impurities attached on the magnetic beads 26 are washed for the third time.

Figure 5A:
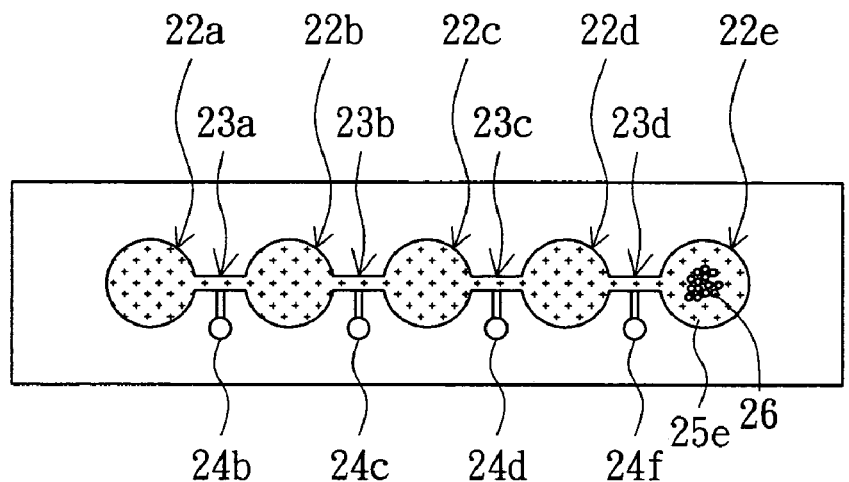
FIG. 5A is a top view showing the state of a magnetic beads of the magnetic bead-based sample separating device in FIG. 3A after having been moved to the last reactor.
Figure 5B:
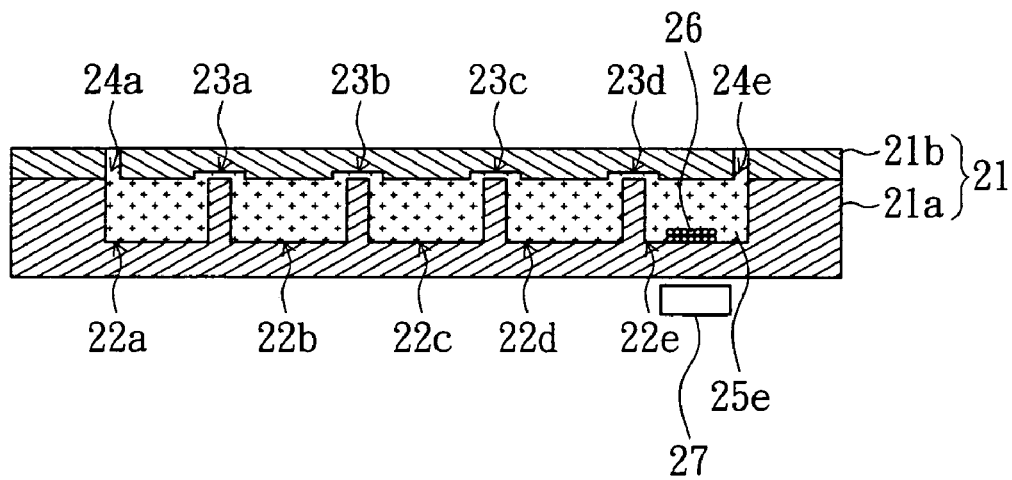
FIG. 5B is a horizontal cross-sectional view of a magnetic bead-based sample separating device in FIG. 5A.

As shown in FIGS. 5A~5B, the magnetic beads 26 with sample extraction are again driven by the above magnetic force to move to the reactor 22e from the reactor 22d via the micro-channel 23d, such that the elution buffer 25e is used to separate the sample extraction from the magnetic beads 26. Furthermore, the magnetic beads 26 that are separated from the sample extraction are attracted on the reactor 22e by the above magnetic force, while both the sample extraction separated from the magnetic beads 26 and the elution buffer 25e are attracted to the outside of the reactor 22e via the opening 24e.

It is noted that the body 21 can be a one-piece structure or a two-piece structure of a base 21a and a cover 21b coupled to the base 21a, wherein the base 21a has the above reactors 22a~22e, the cover 21b has the above openings 24a~24f and the above micro-channels 23a~23d. The base 21a and the cover 21b are made of materials including polymethyl methacrylate (PMMA). However, other suitable materials are also applicable to the present embodiment of the invention. Besides, before the base 21a and the cover 21b are coupled together, the contact surfaces of the base 21a and the cover 21b further have hydrophobic layers disposed therebetween. The hydrophobic layer is made of materials including Teflon. However, other suitable materials are also applicable to the present embodiment of the invention. When manufacturing the magnetic bead-based sample separating device 20, two contact surfaces made of materials including PMMA coated with Teflon are pressed to be coupled together. Teflon enables the PMMA surfaces to be hydrophobic, not only effectively preventing the reactive reagent of the reactor from spilling from the gap between the two PMMA surfaces (the contact surfaces between the base 21a and the cover 21b) when the two PMMA surfaces are moved, but also avoiding the mixture and pollution of different reactive reagents. However, if the base 21a and the cover 21b are not bound by an adhesive (for example, the base 21a and the cover 21b are screwed together), neither of the two PMMA surfaces needs to be coated with Teflon to form a hydrophobic layer.

Besides, the above mixing solution 25a further includes a lysis for damaging the sample to produce a sample extraction, and a binding buffer for binding the magnetic beads 26 and the sample extraction. Moreover, examples of the above sample extraction include protein, deoxyribonucleic acid (DNA), ribonucleic acid (RNA) and so on.

Despite the present embodiment of the invention is exemplified by five reactors 22a~22e with the three reactors 22b~22d respectively receiving the washing buffers 25b~25d for washing the magnetic beads 26, however, the technology of the present embodiment of the invention is not limited thereto. For example, the magnetic bead-based sample separating device 20 of the present embodiment of the invention can be further simplified to employ only three reactors 22a, 22b and 22e and two micro-channels 23a and 23b. That is, the present embodiment of the invention can omit the reactors 22c~22d and the corresponding two micro-channels 23c~23d, and use only one reactor 22b to receive the washing buffer 25b for washing the magnetic beads 26.

The application of the magnetic bead-based sample separating device 20 of the present embodiment of the invention includes the following steps. Firstly, a sample (such as the experimental sample of Salmonella choleraesuis) is mixed with a lysis. After the sample is damaged by the lysis, the magnetic beads 26 and the binding buffer are added, and a mixing solution 25a is added to a reactor 22a via an opening 24a. Next, washing buffers 25b~25d and an elution buffer 25e are sequentially added to corresponding reactors 22b~22e. Adjacent reactors are connected via micro-channels. The micro-channel is a reagent mixing buffer area between two adjacent reactors. Next, the magnetic beads 26 are driven by a magnetic force provided by a magnetic iron 27 moving on the magnetic bead-based sample separating device 20, such that the magnetic beads 26 with sample extraction are sequentially moved to from the first reactor 22a to the last reactor 22e.

Therefore, the magnetic bead-based sample separating device 20 of the present embodiment of the invention is a one-dimensional serial device, wherein each reactor receives a reactive reagent, and a magnetic iron is used to provide a magnetic force for moving the magnetic beads from the first reactor to the second reactor via a micro-channel. The rest may be performed by analogy until the magnetic beads are moved to the last reactor and the entire magnetic bead-based sample extracting process is completed. Besides, the micro-channel functions to reduce the residual of the sample at the terminal reactor. Besides, the micro-channel also functions as a reactive reagent mixing buffer area between two adjacent reactors. Moreover, the reactors are connected by the micro-channels to form an enclosed space.

Second Embodiment

Figure 6A:
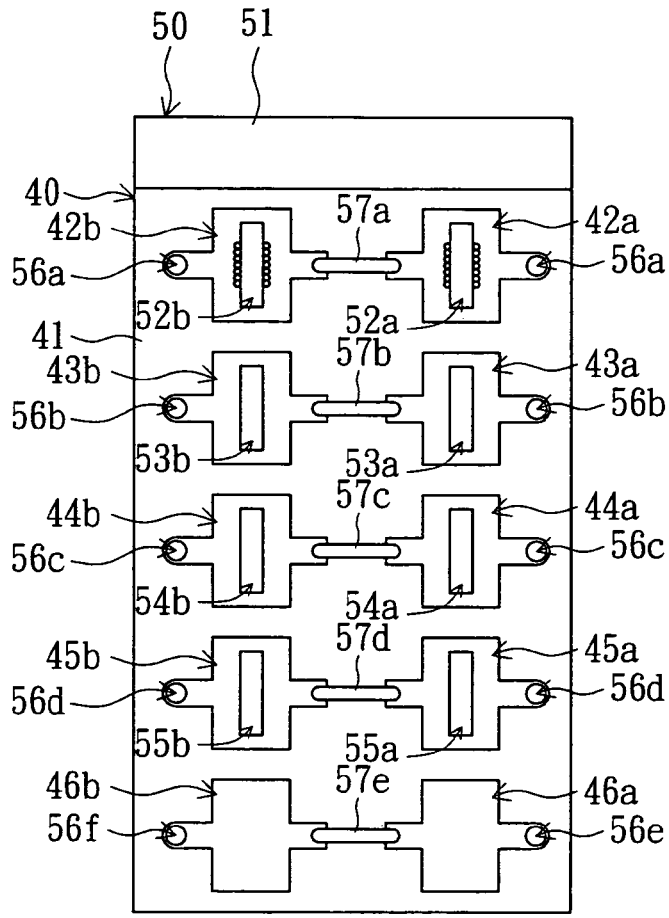
FIG. 6A is a top view of a magnetic bead-based sample separating device according to a second embodiment of the invention.
Figure 6B:
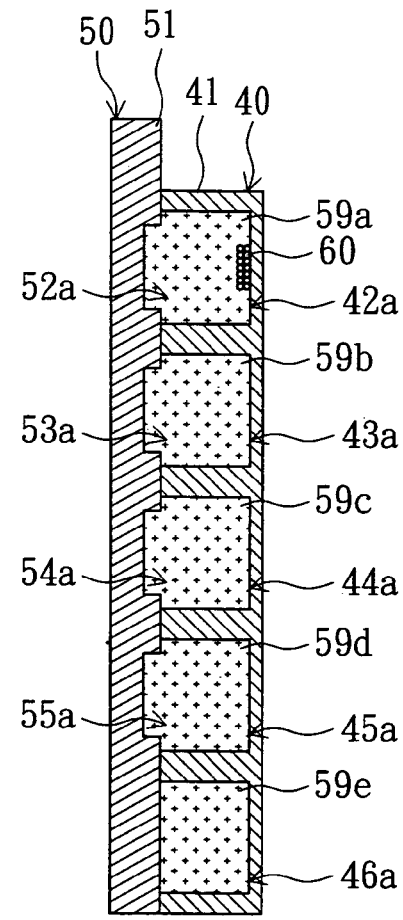
FIG. 6B is a vertical cross-sectional view of a magnetic bead-based sample separating device in FIG. 6A.
Figure 6C:
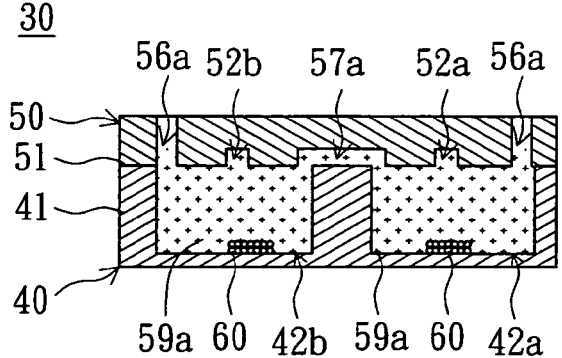
FIG. 6C is a horizontal cross-sectional view of a magnetic bead-based sample separating device in FIG. 6A.

Referring to both FIGS. 6A~6C, FIG. 6A is a top view of a magnetic bead-based sample separating device according to a second embodiment of the invention, FIG. 6B is a vertical cross-sectional view of a magnetic bead-based sample separating device in FIG. 6A, and FIG. 6C is a horizontal cross-sectional view of a magnetic bead-based sample separating device in FIG. 6A. It is noted that FIG. 6B is a cross-sectional view of the rightmost column of the reactor and the micro-channel in FIG. 6A, and FIG. 6C is a cross-sectional view of the topmost column of the reactor and the micro-channel in FIG. 6A. The magnetic bead-based sample separating device 30 includes a reactor array base 40 and a micro-channel array cover 50. The reactor array base 40 includes a base body 41, two reactors 42a and 42b (such as the first reactor) arranged in the same row, two reactors 43a and 43b (such as the second reactor) arranged in the same row, two reactors 44a and 44b arranged in the same row, and two reactors 45a and 45b arranged in the same row and two reactors 46a and 46b (such as the third reactor). The pairs of reactors which are arranged in the same row, including the reactors 42a and 42b, the reactors 43a and 43b, the reactors 44a and 44b, the reactors 45a and 45b, and the reactors 46a and 46b, are disposed on the base body 41, and respectively are horizontally spaced in an equal distance. The reactors 42a, 43a, 44a, 45a and 46a are one-to-one and vertically aligned from top down in the same column. The reactors 42b, 43b, 44b, 45b and 46b are one-to-one and vertically aligned from top down in the same column. The reactors 43a, 44a and 45a are positioned between the reactor 42a and the reactor 46a. The reactors 43b, 44b and 45b are positioned between the reactor 42b and the reactor 46b. The reactor 44a is positioned between the reactor 43a and the reactor 45a. The reactor 44b is positioned between the reactor 43b and the reactor 45b.

The micro-channel array cover 50 is slideably coupled with the reactor array base 40 and includes a cover body 51, two micro-channels 52a and 52b (such as the first micro-channel) arranged in the same row, two micro-channels 53a and 53b (such as the second micro-channel) arranged in the same row, two micro-channels 54a and 54b arranged in the same row, two micro-channels 55a and 55b arranged in the same row and five micro-channels 57a~57e (such as the third micro-channel) sequentially arranged in five rows. The cover body 51 has two openings 56a, two openings 56b, two openings 56c, two openings 56d, two openings 56e and two openings 56f. The reactors 42a and 43a are respectively connected with an opening 56a and an opening 56b (such as the first opening and the second opening). The reactors 42b and 43b are respectively connected with the other opening 56a and the other opening 56b. The reactors 44a and 45a are respectively connected with an opening 56c and an opening 56d. The reactors 44b and 45b are respectively connected with the other opening 56c and the other opening 56d. The reactors 46a and 46b are respectively connected with the openings 56e and 56f (such as the third opening). The micro-channels 52a and 52b, 53a and 53b, 54a and 54b, 55a and 55b and 57a~57e are disposed on the cover body 21 and are horizontally spaced in an equal distance. The micro-channels 52a, 53a, 54a and 55a are one-to-one and vertically aligned from top down in the same column. The micro-channels 52b, 53b, 54b and 55b are one-to-one and vertically aligned from top down in the same column. The micro-channel 57a is positioned between the two micro-channels 52a and 52b. The micro-channel 57b is positioned between the two micro-channels 53a and 53b. The micro-channel 57c is positioned between the two micro-channels 54a and 54b. The micro-channel 57d is positioned between the two micro-channels 55a and 55b. The micro-channel 57e is adjacent to the micro-channel 57d and is positioned under micro-channel 57d in an equal distance. The micro-channels 52a and 52b, 53a and 53b, 54a and 54b and 55a and 55b are vertical micro-channels, while the micro-channels 57a~57e are horizontal micro-channels.

The micro-channel 57a connects the reactors 42a and 42b. The micro-channel 57b connects the reactors 43a and 43b. The micro-channel 57c connects the reactors 44a and 44b. The micro-channel 57d connects the reactors 45a and 45b. The micro-channel 57e connects the reactors 46a and 46b. The reactors 42a and 42b receive a mixing solution 59a via any of the two openings 56a and the micro-channel 57a, wherein the mixing solution 59a at least includes several magnetic beads 60 and a sample extraction bound with the magnetic beads 60. According to the law of connected pipes, the reactors 43a and 43b receive a washing buffer 59b via any of the two openings 56b and the micro-channel 57b. According to the law of connected pipes, the reactors 44a and 44b receive a washing buffer 59c via any of the two openings 56c and the micro-channel 57c. According to the law of connected pipes, the reactors 45a and 45b receive a washing buffer 59d via any of the two openings 56d and the micro-channel 57d. According to the law of connected pipes, the reactors 46a and 46b receive an elution buffer 59e via either of the openings 56e and 56f and the micro-channel 57e. Part of the magnetic beads 60 with sample extraction are driven by a magnetic force to move to the reactor 42b from the reactor 42a via the micro-channel 57a, wherein the magnetic force is exemplified by a magnetic force provided by a magnetic iron. The ways by which the mixing solution 59a, the washing buffers 59b~59d and the elution buffer 59e are respectively received by the reactors 42a and 42b, the reactors 43a and 43b, the reactors 44a and 44b, the reactors 45a and 45b and the reactors 46a and 46b are not limited to the ways disclosed above, any other ways of receiving the mixing solution, the washing buffers and the elution buffer are applicable to the present embodiment of the invention.

As shown in FIGS. 7A~7C, when the micro-channel array cover 40 and reactor array base 50 move relatively by a distance, the micro-channel 52a connects the reactors 42a and 43a, and the micro-channel 53a connects the reactors 43a and 44a. The micro-channel 54a connects the reactors 44a and 45a, and the micro-channel 55a connects the reactors 45a and 46a. Similarly, the micro-channel 52b connects the reactors 42b and 43b, and the micro-channel 53b connects the reactors 43b and 44b. The micro-channel 54b connects the reactors 44b and 45b, and the micro-channel 55b connects the reactors 45b and 46b.

The application of the magnetic bead-based sample separating device 30 in the magnetic bead-based separating technology includes the following steps. Firstly, the magnetic beads 60 with sample extraction are driven by a magnetic force to move to reactors 43a and 43b from reactors 42a and 42b via micro-channels 52a and 52b, such that a washing buffer 59b is used to wash the magnetic beads 60, and the impurities attached on the magnetic beads 60 are washed for the first time. The magnetic force is exemplified by a magnetic force provided by an iron 61.

Next, the magnetic beads 60 with sample extraction are driven by the above magnetic force to move to reactors 44a and 44b from the reactors 43a and 43b via micro-channels 53a and 53b, such that a washing buffer 59c is used to wash the magnetic beads 60, and the impurities attached on the magnetic beads 60 are washed for the second time.

Then, the magnetic beads 60 with sample extraction are driven by the above magnetic force to move to reactors 45a and 45b from the reactors 44a and 44b via micro-channels 54a and 54b, such that a washing buffer 59d is used to wash the magnetic beads 60, and the impurities attached on the magnetic beads 60 are washed for the third time.

Next, the magnetic beads 60 with sample extraction are driven by the above magnetic force to move to reactors 46a and 46b from the reactors 45a and 45b via micro-channel 55a and 55b, such that an elution buffer 59e is used to separate the sample extraction from the magnetic beads 60. Furthermore, the micro-channel array cover 40 and the reactor array base 50 are moved relatively such that the original states as indicated in FIGS. 6A~6B are restored. Meanwhile, the magnetic beads 60 separated from the sample extraction can be attracted by the above magnetic force into the reactors 46a and 46b, while the sample extraction separated form the magnetic beads 60 and the elution buffer 59e are attracted out from the reactors 46a and 46b via the openings 56e~56f.

It is noted that if the reactors in each row are horizontally connected via horizontal micro-channels, then the reactors in each column are unable to be vertically connected via vertical micro-channels. To the contrary, if the reactors in each column are vertically connected via the vertical micro-channels, the reactors in each row are unable to be horizontally connected via the horizontal micro-channels.

Despite the present embodiment of the invention is exemplified by ten reactors 42a and 42b, 43a and 43b, 44a and 44b, 45a and 45b and 46a and 46b with six reactors 43a and 43b, 44a and 44b, 45a and 45b respectively receiving the washing buffers 59b~59d for sequentially washing the magnetic beads 60, however, the technology of present embodiment of the invention is not limited thereto. For example, the magnetic bead-based sample separating device 30 of the present embodiment of the invention can be further simplified to employ only six reactors and seven micro-channels. That is, the present embodiment of the invention can omit the reactors 44a and 44b, 45a and 45b and the corresponding six micro-channels 53a and 53b, 54a and 54b, and 57c and 57d, and use only two reactors 43a and 43b to receive the washing buffer 59b to wash the magnetic beads 60.

The above mixing solution 59a further includes a lysis for damaging sample to produce a sample extraction, and a binding buffer for binding the magnetic beads 60 and the sample extraction. Moreover, the above sample extraction includes protein, deoxyribonucleic acid (DNA), ribonucleic acid (RNA) and so on. The base body 41 and the cover body 51 are made of materials including polymethyl methacrylate (PMMA).

In the present embodiment of the invention, the pipe diameter of micro-channel 57a~57e is larger than the diameter of each of the magnetic beads 60, and the pipe diameter of each of the micro-channels 52a and 52b, 53a and 53b, 54a and 54b and 55a and 55b is also larger than the diameter of each of the magnetic beads 60. Both the pipe diameter of the micro-channels 57a~57e and the pipe diameter of each of the micro-channels 52a and 52b, 53a and 53b, 54a and 54b and 55a and 55b approximately range between 50 μm~500 μm, and the diameter of each of the magnetic beads 60 approximately ranges between 50 nanometer (nm)~40 μm.

The misplacement-type magnetic bead-based sample separating device 30 of the present embodiment of the invention is composed of a serial reactor array base 40 and a micro-channel array cover 50 to form a two-dimensional serial separating device. The reactors of the same row or the column are connected via misplaced micro-channel net movement. When filling a reactive reagent such as a mixing solution, a washing buffer or an elution buffer, the connection among serial reactors of the same column is closed, and the connection among non-serial reactors of the same row for receiving the same reactive reagent is open (as shown in FIGS. 6A~6C). During the magnetic bead-based sample extracting process, if the connection among serial reactors of the same column is open and the connection among non-serial reactors of the row for receiving the same reactive reagent is closed, then the magnetic bead-based sample separating process (as shown in FIGS. 7A~7C) can be activated.

Third Embodiment

Figure 8:
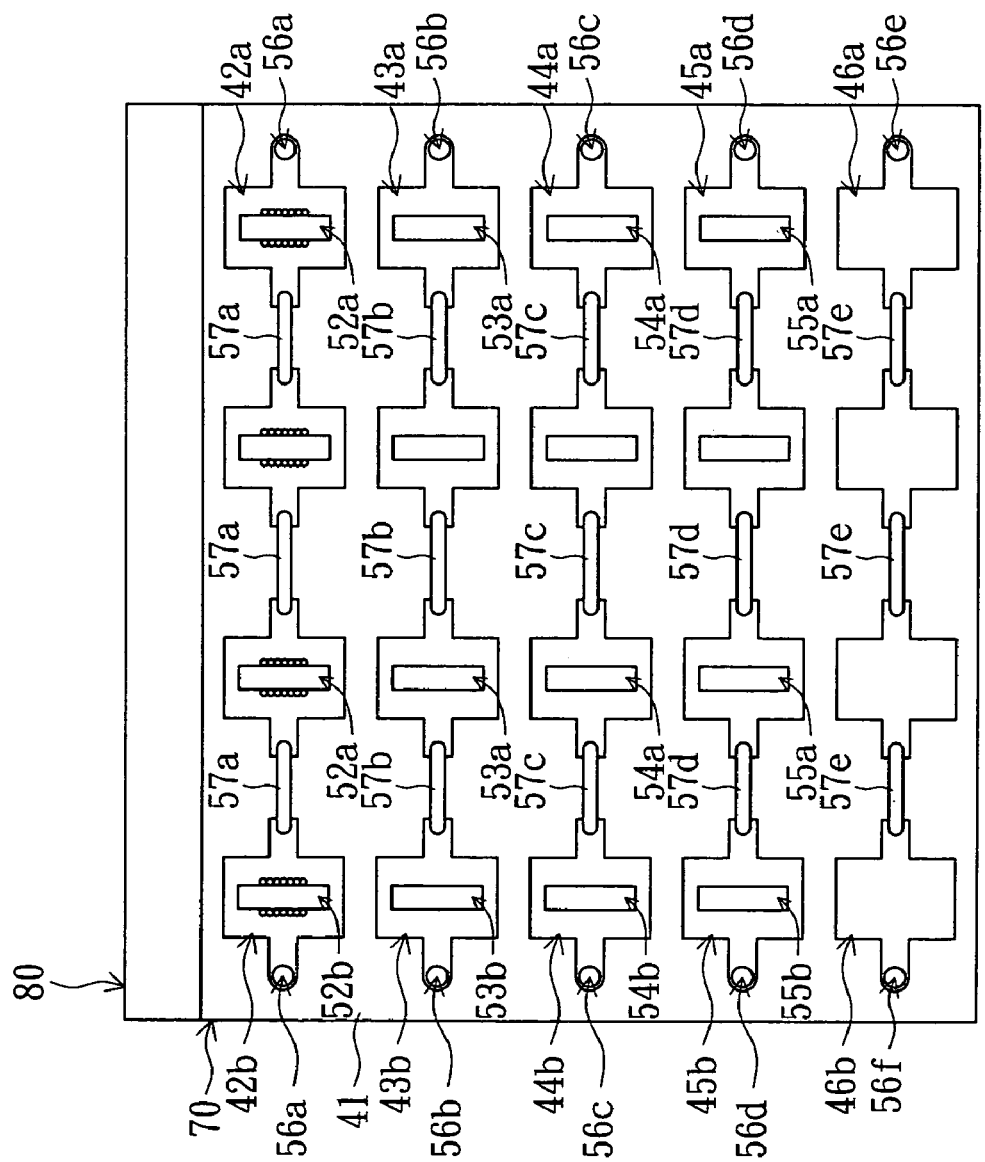
FIG. 8 is a top view of a magnetic bead-based sample separating device according to a third embodiment of the invention.

Referring to FIG. 8, a top view of a magnetic bead-based sample separating device according to a third embodiment of the invention is shown. The magnetic bead-based sample separating device 90 includes a reactor array base 70 and a micro-channel array cover 80. The reactor array base 70 of the present embodiment of the invention can be augmented from the reactor array base 40 of the second embodiment to have more than two rows of reactors. For example, the reactor array base 70 has four rows of reactors, and each row has five reactors. Moreover, the micro-channel array cover 80 of the present embodiment of the invention can also be augmented from the micro-channel array cover 50 of the second embodiment to have more than two rows of vertical micro-channels and more than one row of horizontal micro-channels. For example, the micro-channel array cover 80 can have four rows of vertical micro-channel with each row having four vertical micro-channels, and three rows of horizontal micro-channels with each row having five horizontal micro-channels.

The magnetic bead-based sample separating device disclosed in the above embodiment of the invention employs multiple serial reactors and the misplaced micro-channel net movement, and is capable of filling the reagent and completing the magnetic bead-based sample extracting process synchronously. Consequently, the magnetic beads extracting rate is increased, and the extraction of magnetic beads is enhanced. Besides, the process of the invention is performed at an enclosed space, largely reducing the risk of pollution.

The magnetic bead-based sample separating device of the invention has the following advantages:

1. Replacing repetitive washing, a reactive reagent is used by actively transporting the magnetic beads, such that the manual and tedious steps of quantifying, sucking and receiving the reagent are reduced, and the extracting efficiency of the magnetic beads is increased.

2. The manual and tedious steps in the magnetic bead-based sample extracting process are reduced and the diversity and extraction of the sample is increased by misplaced micro-channel net movement.

3. An enclosed space by serial reactors and micro-channels is formed, such that the pollution risk during the sample separating process is reduced.

Despite the invention is disclosed in the above preferred embodiments, however, the above preferred embodiments are not for limiting the invention.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A magnetic bead-based sample separating device, comprising:
   a body;
   a first reactor disposed inside the body for receiving a mixing solution at least comprising a plurality of magnetic beads and a sample extraction, wherein the sample extraction is bound with the magnetic beads;
   a second reactor disposed inside the body for receiving a washing buffer;
   a third reactor disposed inside the body for receiving an elution buffer, wherein the second reactor is positioned between the first reactor and the third reactor;
   a first micro-channel disposed inside the body for connecting the first reactor and the second reactor; and
   a second micro-channel disposed inside the body for connecting the second reactor and the third reactor;
   wherein the magnetic beads are driven by a magnetic force to move to the second reactor from the first reactor via the first micro-channel for enabling the washing buffer to wash the magnetic beads;
   wherein the magnetic beads are driven by the magnetic force to move to the third reactor from the second reactor via the second micro-channel for enabling the elution buffer to separate the sample extraction from the magnetic beads.

2. The device according to claim 1, wherein the first micro-channel is positioned between an apex of the first reactor and an apex of the second reactor, and the second micro-channel is positioned between the apex of the second reactor and an apex of the third reactor.

3. The device according to claim 2, wherein a pipe diameter of the first micro-channel and a pipe diameter of the second micro-channel are respectively larger than a diameter of each magnetic bead.

4. The device according to claim 3, wherein the pipe diameter of the first micro-channel and the pipe diameter of the second micro-channel range between 50 μm~500 μm.

5. The device according to claim 1, wherein the body further has a base and a cover coupled to the base, the base has the first reactor, the second reactor and the third reactor, and the cover has the first micro-channel and the second micro-channel.

6. The device according to claim 5, wherein the base and the cover are made of materials including polymethyl methacrylate (PMMA).

7. The device according to claim 5, wherein contact surfaces of the base and the cover have hydrophobic layers disposed between the base and the cover.

8. The device according to claim 7, wherein the hydrophobic layer is made of materials including Teflon.

9. The device according to claim 1, wherein the magnetic force is provided by a magnetic iron.

10. The device according to claim 1, wherein the mixing solution further comprises a sample, a lysis for damaging the sample to produce the sample extraction, and a binding buffer for binding the magnetic beads and the sample extraction.

11. The device according to claim 1, wherein the body has a first opening, a second opening, a third opening and a fourth opening, which are respectively connected with the first reactor, the first micro-channel, the second micro-channel, and the third reactor.

12. The device according to claim 11, wherein the magnetic beads are attracted into the third reactor by the magnetic force, and the sample extraction and the elution buffer are attracted out from the third reactor via the fourth opening.

13. A magnetic bead-based sample separating device, comprising:
   a reactor array base, comprising:
      a base body;
      more than two first reactors disposed on the base body and horizontally interspaced;
      more than two second reactors disposed on the base body and horizontally interspaced; and
      more than two third reactors disposed on the base body and horizontally interspaced, wherein the more than two first reactors, the more than two second reactors and the more than two third reactors are correspondingly and vertically aligned, each second reactor is positioned between the corresponding first reactor and the corresponding third reactor; and
   a micro-channel array cover slideably coupled with the reactor the base, the micro-channel array cover comprising:
      a cover body having a first opening, a second opening, and more than two third openings, wherein the first opening and the second opening are respectively connected with the first reactor and the second reactor, while the more than two third openings are correspondingly connected with the more than two third reactors;
      more than two first micro-channels disposed on the cover body and horizontally interspaced;
      more than two second micro-channels disposed on the cover body and horizontally interspaced, wherein the more than two first micro-channels and the more than two second micro-channels are correspondingly and vertically aligned; and
      more than three third micro-channels disposed on the cover body, wherein the two adjacent more than three third micro-channels are respectively positioned between the more than two first micro-channels and between the more than two second micro-channels, the more than three third micro-channels are respectively connected with the more than two first reactors, the more than two second reactors and the more than two third reactors;
   wherein the more than two first reactors are for receiving a mixing solution comprising a plurality of magnetic beads and a sample extraction via the first opening and the corresponding third micro-channel, and the sample extraction is bound with the magnetic beads;
   wherein the more than two second reactors are for receiving a washing buffer via the second opening and the corresponding third micro-channel;
   wherein the more than two third reactors are for receiving an elution buffer via the third opening and the corresponding third micro-channel;
   wherein when the micro-channel array cover and the reactor array base are relatively moved for a distance, each first micro-channel connects the adjacent first reactor and second reactor, and each second micro-channel connects the adjacent second reactor and third reactor;
   wherein the magnetic beads are driven by the magnetic force to move to the more than two second reactor from the more than two first reactors via the more than two first micro-channels for enabling the washing buffer to wash the magnetic beads;

wherein the magnetic beads are driven by the magnetic force again to move to the more than two third reactors from the more than two second reactors via the more than two second micro-channels for enabling the elution buffer to separate the sample extraction from the magnetic beads.

14. The device according to claim 13, wherein a pipe diameter of each first micro-channel and a pipe diameter of each second micro-channel are respectively larger than a diameter of each magnetic bead.

15. The device according to claim 14, wherein the pipe diameter of each first micro-channel and each second micro-channel ranges between 50 μm~500 μm.

16. The device according to claim 13, wherein a pipe diameter of the third micro-channel for connecting the more than two first reactors is larger than a diameter of each magnetic bead.

17. The device according to claim 16, wherein the pipe diameter of the third micro-channel for connecting the more than two first reactors ranges between 50 μm~500 μm.

18. The device according to claim 13, wherein the base body and the cover body are made of materials including polymethyl methacrylate (PMMA).

19. The device according to claim 13, wherein the mixing solution further comprises a sample, a lysis for damaging the sample to produce the sample extraction, and a binding buffer for binding the magnetic beads and the sample extraction.

20. The device according to claim 13, wherein the magnetic beads are attracted into the more than two third reactors by the magnetic force, and the sample extraction and the elution buffer are attracted out from the more than two third reactors via the more than two third openings.

* * * * *